United States Patent [19]

Beige et al.

[11] 4,182,318
[45] Jan. 8, 1980

[54] METHOD AND BRACE FOR TREATING EPICONDYLITIS

[76] Inventors: Günter Beige; Horst Braunberger, both of Bahnhofstrasse 49, 6680 Neunkirchen, Fed. Rep. of Germany

[21] Appl. No.: 784,449

[22] Filed: Apr. 4, 1977

[30] Foreign Application Priority Data

Aug. 6, 1976 [DE] Fed. Rep. of Germany ....... 2635426

[51] Int. Cl.² .......................... A61F 5/01; A61F 13/10
[52] U.S. Cl. ........................................ 128/77; 128/165
[58] Field of Search ............ 128/77, 165, 80 R, 80 C, 128/327; 273/189 R, 189 A

[56] References Cited

U.S. PATENT DOCUMENTS

| | | | |
|---|---|---|---|
| 2,179,903 | 11/1939 | Spears | 128/80 C |
| 3,581,741 | 6/1971 | Rosman | 128/80 C |
| 3,669,105 | 6/1972 | Castiglia | 128/80 C |
| 4,027,666 | 6/1977 | Marx | 128/165 |

Primary Examiner—John D. Yasko
Attorney, Agent, or Firm—Robert W. Beach; Ward Brown

[57] ABSTRACT

A brace includes a U-shaped resilient band clamp having clamp jaws with inner facing pressing surfaces for applying pressure to the lateral and medial aspects of the elbow region of an arm. The pressing surface of one of the clamp jaws is larger than the pressing surface of the other clamp jaw. The inner periphery of the clamp band is padded and the clamp carries a retaining strap for holding it on the elbow region of an arm afflicted with epicondylitis to apply pressure on the arm muscles and their associated tendons near their origins on the humeral epicondyles.

8 Claims, 2 Drawing Figures

METHOD AND BRACE FOR TREATING EPICONDYLITIS

BACKGROUND OF THE INVENTION

1. Field of the Invention

The present invention relates to braces, particularly braces for the treatment of epicondylitis.

2. Prior Art

Epicondylitis is a pain syndrome affecting the elbow region. The affliction is accompanied by inflamation of the common extensor tendon or common flexor tendon near its point of attachment to the lateral or medial epicondyle and, sometimes, by inflamation of adjacent tissues. A brief description of epicondylitis is contained in *Current Diagnosis & Treatment* by M. Krupp and M. Chatton, published by Lange Medical Publications (1973) at page 475. As there noted, up to now treatment of the affliction has been by injection of hydrocortisone; by immobilization of the affected elbow by a splint or cast; by surgery; or by simple rest of the affected arm, with special emphasis on avoidance of grasping motions. Treatment by standard bandages, such as those commonly used to treat muscle strains and pulls, encircling the elbow region and/or forearm and applying substantially uniform pressure has been tried without demonstrable success.

SUMMARY OF THE INVENTION

It is an object of the present invention to provide a brace for the treatment of epicondylitis which brace will change the pulling directions of the muscles and their associated tendons having their origins at the humeral epicondyles.

Another object is to provide a clamping brace which can be used without severely limiting the mobility of the clamped region.

A further object is to provide a brace which can be easily applied to and removed from an elbow region.

It is also an object to provide a brace which will remain reliably in place after it has been applied.

Another object is to provide a brace which will not restrict the flow of blood between the upper arm and the forearm when such brace is applied to an elbow region.

The foregoing objects can be accomplished by providing a brace which includes a resilient band clamp having opposed clamp jaws. The inner surfaces of the clamp jaws provide pressing surfaces for applying pressure to the lateral and medial aspects of the elbow region of an arm. Such pressing surfaces can be applied distal to the epicondyles of an arm affected by epicondylitis. The pressure exerted by the clamp jaws on a specific area and the size of the area clamped can be varied by providing clamping surfaces of different sizes. In a preferred embodiment of the invention, the clamp inner periphery is padded and the clamp carries a retaining strap to help hold the clamp on an afflicted arm.

DETAILED DESCRIPTION

Figure 1:
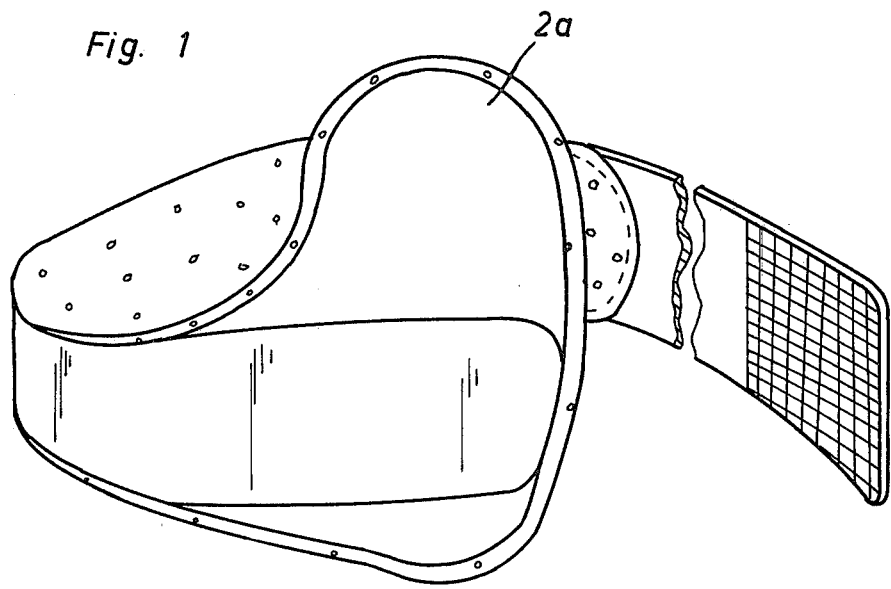
FIG. 1 is a perspective of a brace in accordance with the present invention.
Figure 2:
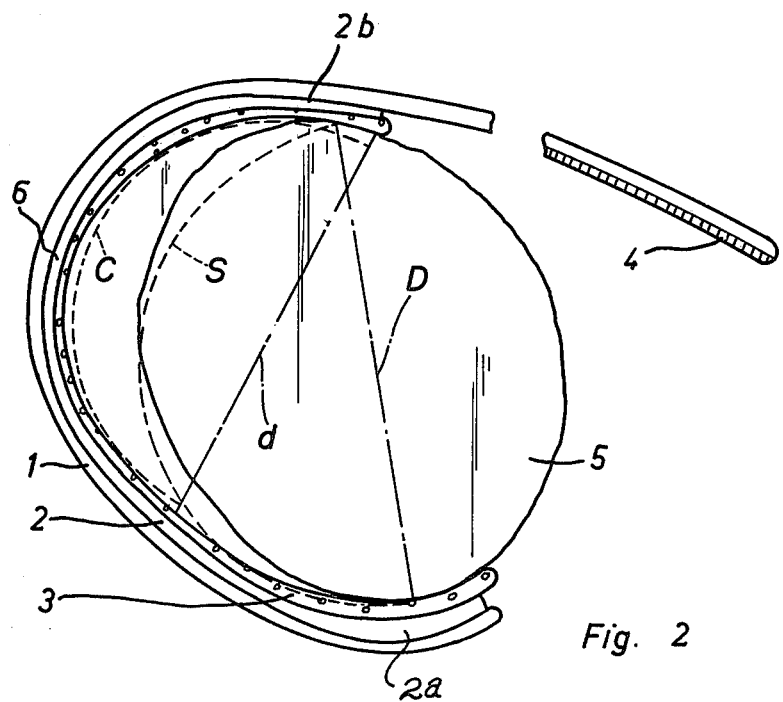
FIG. 2 is a plan of the brace of FIG. 1 as applied to an arm with the arm shown in phantom section.

The preferred embodiment of the brace of the present invention shown in FIGS. 1 and 2 includes a U-shaped resilient band clamp 2 formed of spring strip material, such as steel or plastic. The clamp has opposed end portions or clamp jaws 2a and 2b connected by a spring bow portion 6. The clamp jaws form inner pressing surfaces for applying pressure to an object placed between the clamp jaws, which object has a width greater than the distance between the jaws when the clamp is relaxed.

The inner periphery of band 2 is lined with a padding layer 3. The brace can be applied to an elbow afflicted with epicondylitis so that the clamp jaws exert inward pressure on the lateral and medial aspects of an arm 5. The brace should be applied to embrace the elbow at a location where pressure will be exerted on the arm muscles and their associated tendons near their points of attachment to the epicondyles. Such pressure will cause a change in the pulling directions of the muscles and tendons. Since epicondylitis usually affects either the lateral or medial side of an elbow region but not both, it is desirable for one of the clamp jaws to have a larger pressing surface than the other clamp jaw. The larger jaw can engage the unaffected side of an afflicted elbow and its larger pressing surface will help prevent distortion of underlying tissue. The smaller jaw pressing surface can apply a more concentrated pressure on a smaller specific area. The larger jaw pressing surface could be, for example, six or seven centimeters wide and the smaller jaw pressing surface two or three centimeters wide.

A retaining strap 1 to hold the brace in place as the arm is flexed is bonded to the outer periphery of the clamp band 2 or otherwise attached to the band and includes a flexible free end portion 4 projecting beyond one of the clamp jaws. The strap is long enough so that the end portions of the strap can overlap when it is wrapped around the arm. Such overlapping portions can be secured in overlapping relationship by having mutually adherent surfaces, such as a hook and pile fastener of the type disclosed in U.S. Pat. No. 2,717,437 and sold under the trademark Velcro. Closely spaced nylon hooks are provided on the inner surface of the free end portion and such free end portion is long enough to close the mouth of the clamp and overlap a pile surface on the exterior of the other strap end. A brace which has been applied to an afflicted arm will be held in place by the clamp jaws gripping opposite sides of the elbow and by the retaining strap closing the mouth of the clamp so that the arm is completely encircled by the brace. As shown in FIG. 2, the clamp bow portion 6 preferably is spaced from the arm. As shown in FIG. 2, the substantially semicircular curve C of the major part of the clamp bow portion 6 subtended by diameter d is much sharper than the curvature of the semicircle S subtended by the diameter D connecting the pressing surfaces of the jaws 2a and 2b pressing against the opposite sides of the elbow. Hence, the mobility of the clamped region is not unduly restricted and substantial pressure can be exerted by the clamp jaws without constricting the flow of blood between the upper arm and the forearm. At the same time the clamp is not unduly bulky and does not project excessively laterally beyond the arm so that it can be received readily within the average garment sleeve.

We claim:

1. A brace for treating an arm afflicted with epicondylitis comprising a resilient U-shaped spring band having opposite end portions forming two opposed jaws, one of said jaws having a pressing surface engageable with the medial aspect of the elbow region of the arm and the other of said jaws having a pressing surface engageable with the lateral aspect of the elbow region of the arm, said clamp further having a bow portion connecting said jaws the major part of which bow portion is of a size and shape to be spaced from the arm when said pressing surfaces of said jaws are in engagement, respectively, with the lateral and medial aspects of the arm elbow region, said pressing surfaces of said jaws normally being spaced apart a distance less than the distance between the lateral and medial aspects of the arm elbow region but being spreadable for engagement with such aspects for applying substantial pressure thereon due to the resiliency of said spring band for applying pressure on the arm muscles and their associated tendons to change the pulling directions of such muscles and tendons.

2. The brace defined in claim 1, the pressing surfaces of the clamp jaws being directly opposed and the pressing surface of one clamp jaw being larger than the pressing surface of the other clamp jaw.

3. The brace defined in claim 1, the inner periphery of the U-shaped spring band being padded.

4. The brace defined in claim 1, including a retaining strap bridging between the ends of the spring band.

5. The brace defined in claim 1, the spring band including a bow portion a major part of which is curved substantially more sharply than the curvature of a semicircle subtended by a diameter connecting the pressing surfaces of the jaws when such pressing surfaces are in engagement, respectively, with the lateral and medial aspects of the arm elbow region.

6. A brace for treating an arm afflicted with epicondylitis comprising a clamp including two opposed clamp jaws, one of said jaws having a pressing surface engageable with the medial aspect of the elbow region of the arm and the other of said jaws having a pressing surface engageable with the lateral aspct of the elbow region of the arm for applying pressure on the arm muscles and their associated tendons to change the pulling directions of such muscles and tendons, said clamp further including a bow portion connecting said jaws the major part of which bow portion is of a size and shape to be spaced from the arm when said pressing surfaces of said jaws are in engagement, respectively, with the lateral and medial aspects of the arm elbow region, said pressing surfaces of said clamp jaws being directly opposed and the pressing surface of one clamp jaw being larger than the pressing surface of the other clamp jaw.

7. A brace for treating an arm afflicted with eipcondylitis comprising a clamp including two opposed clamp jaws, one of said jaws having a pressing surface engageable with the medial aspect of the elbow region of the arm and the other of said jaws having a pressing surface engageable with the lateral aspect of the elbow region of the arm for applying pressure on the arm muscles and their associated tendons to change the pulling directions of such muscles and tendons, said clamp further including a bow portion connecting said jaws the major part of which bow portion is of a size and shape to be spaced from the arm when said pressing surfaces of said jaws are in engagement, respectively, with the lateral and medial aspects of the arm elbow region, a major part of said bow portion being curved substantially more sharply than the curvature of a semicircle subtended by a diameter connecting said pressing surfaces of said jaws when said pressing surfaces are in engagement, respectively, with the lateral and medial aspects of the arm elbow region.

8. The method of treating an arm afflicted with epicondylitis which comprises gripping the lateral and medial aspects of the elbow region of the arm adjacent to the humerous epicondyles between the jaws of a clamp having a bow portion connecting the clamp jaws which bow portion is of a size and shape to be spaced from the arm when such jaws are thus gripping such lateral and medial arm elbow region aspects, and thereby forcing a change in the pulling directions of the muscles and associated tendons having their origins at such epicondyles without applying pressure to a circumferential portion of such arm elbow region between its lateral and medial aspects gripped by the clamp jaws.

* * * * *